United States Patent [19]

Norris

[11] 3,968,126
[45] July 6, 1976

[54] FERROCENE DERIVATIVES AND THEIR PREPARATION

[75] Inventor: William P. Norris, Ridgecrest, Calif.

[73] Assignee: The United States of America as represented by the Secretary of the Navy, Washington, D.C.

[22] Filed: Mar. 22, 1974

[21] Appl. No.: 454,036

[52] U.S. Cl.................. 260/346.1 M; 260/439 CY; 149/109.4; 149/109.6
[51] Int. Cl.².................................... C07D 307/00
[58] Field of Search.............. 260/346.1 M, 439 CY; 149/109.4, 109.6

[56] References Cited
UNITED STATES PATENTS 3,864,178    2/1975    Rudy et al. ................. 149/109.6 X

*Primary Examiner*—Stephen J. Lechert, Jr.
*Attorney, Agent, or Firm*—R. S. Sciascia; Roy Miller; Lloyd E. K. Pohl

[57] ABSTRACT

A series of hydroxy containing ferrocene derivatives are prepared. The ferrocene derivatives are useful as burning rate catalysts in solid rocket propellants.

10 Claims, No Drawings

FERROCENE DERIVATIVES AND THEIR PREPARATION

BACKGROUND OF THE INVENTION

1. Field of the Invention.

This invention relates to ferrocene derivatives and to methods for their preparation. More particularly, this invention relates to ferrocene derivatives which contain at least one hydroxy group and to methods for their preparation.

2. Description of the Prior Art.

The use of ferrocene and ferrocene derivatives as burning rate modifiers in solid rocket propellants is well known. It is further well known that, unless a ferrocene derivative can be somehow chemically tied into the solid propellant grain it tends to migrate to the surface when the grain is stored. Migration is, of course undesirable because, in order to provide its burning rate modification properties, the modifier should be evenly spread throughout the grain.

One well known way to chemically tie ferrocene derivatives into solid propellant grains and prevent migration is to utilize hydroxy containing derivatives. When a hydroxy containing derivative is added to a solid propellant mix which contains an isocyanate curing agent, the hydroxy groups react with isocyanate groups and form chemical bonds which tie the ferrocene derivative into the grain and prevent migration. It is, accordingly, the object of this invention to provide new ferrocene derivatives which contain hydroxy groups and can be chemically tied into a solid propellant which contains, as the curing agent, an isocyanate. Another object of this invention is to provide methods by which the hydroxy containing ferrocene derivatives described herein can be prepared.

SUMMARY OF THE INVENTION

Ferrocene and 1,6-dioxa[4,4]spirononane are the starting compounds in the preparation of the series of hydroxy containing ferrocene derivatives of this invention. Reaction of the starting compounds in the presence of methylene chloride solvent and either boron trifluoride etherate or aluminum chloride catalyst yields 2-ferrocenyl-2-(3-hydroxypropyl)tetrahydrofuran. Reaction of 2-ferrocenyl-2-(3-hydroxypropyl)tetrahydrofuran with methylmagnesium iodide in benzene yields 4-methyl-4-ferrocenylheptane-1,7-diol. Reaction of 2-ferrocenyl-2-(3-hydroxypropyl)tetrahydrofuran with ferrocene in methylene chloride in the presence of trifluoroacetic acid yields 4,4-diferrocenylheptane-1,7-diol. Treatment of 2-ferrocenyl-2-(3-hydroxypropyl)-tetrahydrofuran with trifluoroacetic acid and then water yields 4-ferrocenyl-3-heptene-1,7-diol. Reaction of 1,6-dioxa[4,4]spirononane with ferrocene in methylene chloride in the presence of trifluoroacetic acid yields a mixture of 4,4-diferrocenylheptane-1,7-diol and 1,1'-bis[4-(4-ferrocenyl-1,-7-dihydroxyheptyl)]ferrocene which can be separated from each other. Each of the above-named ferrocene derivatives is useful in itself as a burning rate catalyst and 2-ferrocenyl-2-(3-hydroxypropyl)tetrahydrofuran is useful as an intermediate in preparing other ferrocene derivatives in the series.

DESCRIPTION OF THE PREFERRED EMBODIMENT 1,6-Dioxaspiro[4,4]spirononane has the structure:

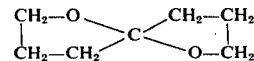

and is sometimes hereinafter referred to as I. 2-Ferrocenyl-2-(3-hydroxypropyl)tetrahydrofuran has the structure:

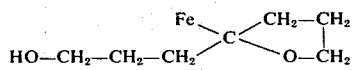

and is sometimes hereinafter referred to as II. 4-Methyl-4-ferrocenylheptane-1,7-diol has the structure:

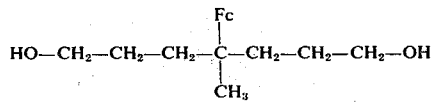

and is sometimes hereinafter referred to as III. 4,4-Diferrocenylheptane-1,7-diol has the structure:

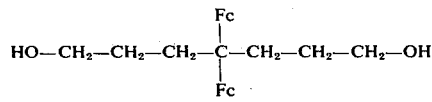

and is sometimes hereinafter referred to as IV. 4-Ferrocenyl-3-heptene-1,7-diol has the structure:

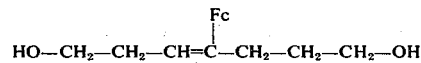

and is sometimes hereinafter referred to as V. 1,1'-Bis[4-(4-ferrocenyl-1,7-dihydroxyheptyl)]ferrocene has the structure:

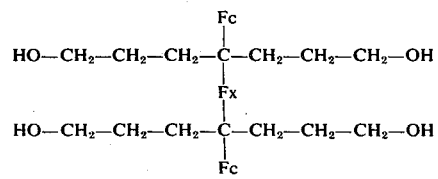

and is sometimes referred to as VI. As used in this disclosure the symbol Fc- means

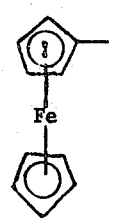

and the symbol -Fx- means

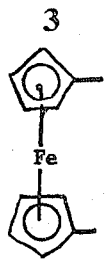

EXAMPLE 1

Preparation of 2-ferrocenyl-2-(3-hydroxypropyl)tetrahydrofuran (II). Ferrocene, 7.44 g (0.040 mole), and 1,6-dioxaspiro-[4,4]-nonane (I), 1.28 g (0.010 mole), were dissolved in 100 ml of methylene chloride and 3.6 ml (0.03 mole) of boron trifluoride etherate [$BF_3 O(Et)_2$] was added with stirring. After 2 hours of stirring, the reaction mixture was poured onto a dry alumina column (5 cm by 25 cm). Unreacted ferrocene, 6.3 g, was eluted from the column using ethylene dichloride. The chromatogram was then developed with a 1 to 1 mixture of ether (ethyl) and ethylacetate. The principal band (middle portion of the column) was cut out and extracted with methyl alcohol to give 1.72 g (55% yield) of II, mp 50°–53°C, after recrystallization from a 1 to 1 mixture of pentane and cyclohexane.

Anal. Calcd. for $C_{17}H_{22}O_2Fe$: C, 64.98; H, 7.06; Fe, 17.78. Found: C, 64.95; H, 6.81; Fe, 17.53. The mass spectrograph of II showed a strong parent ion at m/e 314.

EXAMPLE 2

Preparation of 2-ferrocenyl-2-(3-hydroxypropyl)tetrahydrofuran (II). Aluminum chloride, 3.0 g (0.023 mole), was suspended in 100 ml of methylene chloride. Ferrocene, 14.8 g (0.080 mole), and 1.30 g (0.010 mole) of I were dissolved in 100 ml of methylene chloride and added, dropwise, over 30 minutes to the stirred aluminum chloride suspension. The reaction mixture was stirred for 16 hours at room temperature and then poured into ice and water. A green color developed. The green color was removed by adding ascorbic acid (a reducing agent which reduced ferricinium ion present in the mixture—the cause of the green color). The organic phase was separated, washed once with saturated sodium chloride solution and poured onto a dry 5 cm by 40 cm alumina column. Unreacted ferrocene was eluted with ethylene dichloride and the chromatogram was developed with 25% by volume ethyl acetate in ethylene dichloride. The large yellow band of the chromatogram was extracted with methyl alcohol to give 2.7 g (86% yield) of II. (Analysis confirmed as in Example 1.)

EXAMPLE 3

Preparation of 4-methyl-4-ferroenylheptane-1,7-diol (III). Magnesium, 1.2 g (0.050 mole), was reacted with 7.1 g (0.050 mole) of methyl iodide in 25 ml of ether to form a solution of the Grignard reagent $CH_3MgI$. 2-Ferrocenyl-2-(3-hydroxypropyl)tetrahydrofuran (II), 1.08 g (0.0034 mole), was dissolved in 25 ml ether and added to the Grignard solution. A yellow precipitate formed immediately and then dissolved. Twenty five ml of dry benzene was added and the ether evaporated under reduced pressure. The benzene solution was refluxed for 2.5 hours. Ice water was added to destroy excess Grignard reagent and then 6N HCl was added to dissolve the magnesium salts. The benzene phase was separated and washed with saturated aqueous sodium chloride. The washed benzene phase was then poured onto a dry 3.6 cm by .25 cm alumina column. The chromatogram was developed with ethyl acetate. The most rapidly moving band contained 0.46 g of II. The more slowly moving band was cut out of the column and extracted with methanol to give 0.38 g of III, mp 109°–110°C. Recrystallization from carbon tetrachloride raised the mp to 111°–112°C.

Anal. Calcd. for $C_{18}H_{26}O_2Fe$: C, 65.46; H, 7.94; Fe, 16.91. Found: C, 65.44; H, 8.26; Fe, 16.76. The mass spectrograph of III showed a strong parent ion at m/e 330.

EXAMPLE 4

Preparation of 4,4-diferrocenylheptane-1,7-diol (IV). One gram of 2-ferrocenyl-2-(3-hydroxypropyl)tetrahydrofuran (II) was dissloved in 10 ml of trifluoroacetic acid at 25°C for 2 hours. The trifluoroacetic acid was removed under reduced pressure at 25°C and ferrocene, 5.41 g (0.032 mole), dissolved in 25 ml of methylene chloride, was added to the residue. The solution was stirred 40 hours at 25°C and then treated with 50 ml of $H_2O$ and enough ascorbic acid solution (drop by drop) to reduce the ferricinium ion present. The phases were separated and the aqueous phase was extracted with 25 ml of methylene chloride. The methylene chloride phases were combined and dried over calcium chloride. The solvent ($CH_2Cl_2$) was removed under reduced pressure and the residue was heated at 175°/0.25 mm pressure of 15 minutes to remove residual unreacted ferrocene. The nonvolatile residue was then dissolved in a 2% methyl alcohol in ethyl acetate solution and chromatographed on a dry 3.6 cm by 25 cm alumina column. Extraction of the major yellow band with methyl alcohol gave 1.1 g (69% yield) of 4,4-diferrocenylheptane-1,7-diol (IV). Recrystallization from benzene gave a mp of 168°–171°C. An additional recrystallization from methyl alcohol gave a mp of 169°–171°C.

Anal. Calcd. for $C_{27}H_{32}Fe_2O_2$: C, 64.82; H, 6.45; Fe, 22.33. Found: C, 64.65; H, 6.50; Fe, 22.24. The mass spectrum showed a strong parent ion at m/e 500.

EXAMPLE 5

Preparation of 4-ferrocenyl-3-heptene-1,7-diol (V). 2-Ferrocenyl-2-(3-hydroxypropyl)tetrahydrofuran (II), 20.5 g (0.065 mole), was dissolved in 100 ml of trifluoacetic acid at 25°C with external cooling (in an ice bath). After 5 hours about half of the trifluoroacetic acid was removed under reduced pressure at 25°C. The residue was dissolved in 200 ml of tetrahydrofuran (THF). Then 100 ml of 6N NaOH was added with cooling and the mixture was stirred overnight. The THF phase was separated and the THF removed under reduced pressure. The product crystallized out in the form of plates. The plates were suspended in 500 ml of water, filtered and then washed twice on the filter with 50 ml portions of water. The wet cake was removed from the filter, triturated with 50 ml of ether and then filtered to give 11.0 grams of V, mp 85°–88°C. An additional 2.0 g of material, mp 85°–88°C, was recovered from the liquid phases to give a total yield of 4-ferrocenyl-3heptene-1,7-diol of 13.0 g (63% yield).

Anal. Calcd. for $C_{17}H_{22}FeO_2$: C, 64.98; H, 7.06; Fe, 17.78. Found: C, 65.03; H, 7.00; Fe, 17.57.

EXAMPLE 6

Preparation of 4,4-diferrocenylheptane-1,7-diol (IV), and 1,1'-bis[4-(4-ferrocenyl-1,7-dihydroxyheptyl)]ferrocene (VI). Ten grams of ferrocene and 2.0 g. of I were dissolved in 40 ml of dichloromethane. To this was added a mixture of 6.6 g of trifluoroacetic anhydride and 8.0 g of trifluoroacetic acid as catalyst. The solution was mixed and allowed to stand at 25°C. A nitrogen atmosphere was maintained in the reaction vessel during mixing and during the subsequent reaction. After 16 hours, 100 ml of water was stirred with the brown colored reaction mixture and enough ascorbic acid was added to discharge the green color of the aqueous phase and to turn the organic phase orange in color. The phases were separated and the organic phase was stirred with another 100 ml of water and separated. Dichloromethane was removed from the organic phase under reduced pressure and the residue was dissolved in 100 ml of methanol containing 2 ml of water and 2.0 g of potassium hydroxide. The solution was stirred for 30 minutes and then the methanol and water were removed under reduced pressure. The residue was extracted with (dissolved in) 700 ml of hot ethylene dichloride and filtered. The cooled filtrate was poured onto a dry 36 mm by 240 mm alumina column. Unreacted ferrocene, 5.0 g, was eluted from the column with ethylene dichloride. Using 2% methanol in ethylene dichloride, 5.8 g of a mixture of IV, V and other byproducts were eluted. Recrystallization of this mixture from ethylene dichloride gave 4.6 g (59% yield) of 4,4-diferrocenylheptane-1,7-diol, mp 166°–168°C. Another recrystallization raised the mp to 168°–170°C.

Anal. Calcd. for $C_{27}H_{32}Fe_2O_2$: C, 64.82; H, 6.45; Fe, 22.33. Found: C, 64.65; H, 6.50; Fe, 22.24.

Further elution of the alumina column with 6% methanol in ethylene dichloride gave 1.2 g of 1,1'-bis[4-(4-ferrocenyl-1,7-dihydroxyheptyl)]ferrocene (VI). Recrystallization from methanol gave 0.8 g (12% yield) of VI, mp 202°–204°C.

Anal. Calcd. for $C_{44}H_{54}Fe_3O_4$: C, 64.89; H, 6.68; Fe, 20.57. Found: C, 64.87; H, 6.70; Fe, 20.11.

In this preparation trifluoroacetic acid alone may be used as the catalyst in lieu of the combination of trifluoroacetic acid and trifluoroacetic anhydride recited above with almost equally good results.

In the foregoing Examples, stirring times, reflux times, etc. are recited fairly specifically. The times recited are the times which produced the best yields. However, a range of times in lieu of the specific times recited is permissible. It will be apparent to organic chemists that not allowing a reaction to take place for a long enough period of time will result in a reduced yield and that allowing a reaction mixture to stand after the reaction is completed serves no purpose.

As in the case of times, the reagents percentages can be varied somewhat and still produce almost equally good results.

Each of the ferrocene derivatives of this invention (II, III, IV, V and VI) can be chemically tied into a solid rocket propellant which utilizes an isocyanate curing agent by placing the derivative in the mix so that the hydroxy groups of the derivative will react with isocyanate groups of the curing agent. It will be obvious to those knowledgeable in the propellant arts that compound IV is the most desirable because of its two ferrocenyl groups. However, it will further be obvious that all of the derivatives will add some tied in iron to act as a burning rate modifier.

In addition to being useful as burn rate modifiers, the ferrocene derivatives of this invention may also find use in other areas. For example, ferrocene derivatives are often used as antioxidants, antiknock agents and in a multitude of other areas. The derivatives of this invention may, accordingly, find use in such areas.

What is claimed is:
1. 2-Ferrocenyl-2-(3-hydroxypropyl)tetrahydrofuran.
2. 4-Methyl-4-ferrocenylheptane-1,7-diol.
3. 4,4-Diferrocenylheptane-1,7-diol.
4. 4-Ferrocenyl-3-heptene-1,7-diol.
5. 1,1'-Bis[4-ferrocenyl(1,7-dihydroxy-4-heptyl)]ferrocene.
6. A method for preparing 2-ferrocenyl-2-(3-hydroxypropyl)-tetrahydrofuran, said method comprising:
   a. forming a reaction mixture which contains 1,6-dioxaspiro[4,4]nonane, ferrocene, methylene chloride solvent and a catalyst selected from boron trifluoride etherate and aluminum chloride;
   b. stirring the reaction mixture;
   c. pouring the reaction mixture over an alumina column; and
   d. recovering 2-ferrocenyl-2-(3-hydroxypropyl)tetrahydrofuran from the column by extracting with methyl alcohol.
7. A method for preparing 4-methyl-4-ferrocenylheptane-1,7-diol, said method comprising the steps of:
   a. reacting a reaction mixture of 2-ferrocenyl-2-(3-hydroxypropyl)tetrahydrofuran, methylmagnesium iodide and ether;
   b. adding benzene to the reaction mixture;
   c. removing the ether from the reaction mixture by evaporation;
   d. refluxing the reaction mixtures;
   e. destroying excess methylmagnesium chloride and forming an aqueous phase and an organic phase by adding water to the reaction mixture;
   f. separating the organic phase from the aqueous phase by pouring; and
   g. pouring the organic phase over an alumina column and recovering 4-methyl-4-ferrocenylheptane-1,7-diol therefrom by extraction with methanol.
8. A method for preparing 4,4-diferrocenyl-1,7-diol, said method comprising the steps of:
   a. forming a reaction mixture containing 2-ferrocenyl-2-(3-hydroxypropyl)tetrahydrofuran, ferrocene and methylene chloride;
   b. reacting the reaction mixture;
   c. removing the methylene chloride from the reaction mixture by evaporation and forming a residue;
   d. heating the residue to remove any unreacted ferrocene;
   e. dissolving the residue in ethyl acetate to form a solution; and
   f. pouring the solution over an alumina column and extracting 4,4-diferrocenyl-1,7-diol therefrom with methyl alcohol.
9. A method for preparing 4-ferrocenyl-3-heptene-1,7-diol, said method comprising the steps of:
   a. dissolving 2-ferrocenyl-2-(3-hydroxypropyltetrahydrofuran in trifluoroacetic acid to form a solution;

b. removing the trifluoroacetic acid by reduced pressure to form a residue;
c. dissolving the residue in tetrahydrofuran to form a second solution;
d. adding NaOH to the second solution, stirring and forming an organic phase and a non-organic phase;
e. separating the organic phase from the non-organic phase by pouring; and
f. separating the solent from the organic phase by reduced pressure to leave crysallized 4-ferrocenyl-3-heptene-1,7-diol as the product.

10. A method for preparing 1,1'-bis[4-(4-ferrocenyl-1,7-dihydroxyheptyl)]ferrocene, said method comprising the steps of:
   a. forming a reaction mixture containing 1,6-dioxa[4,4]spirononane and ferrocene as reactants, dichloromethane as a solvent and trifluoroacetic anhydride and trifluoroacetic acid as catalytic material;
   b. allowing the reaction mixture to react;
   c. removing the dichloromethane from the reaction mixture by reduced pressure to leave a residue;
   d. dissolving the residue in a mixture of methanol, water and potassium hydroxide to form a solution;
   e. removing the methanol and water from the solution by reduced pressure to form a residue;
   f. dissolving the residue in ethylene chloride to form a solution;
   g. pouring the solution over an alumina column and removing all materials which are not 1,1-bis[4-(4-ferroceny-1,7-dihydroxylheptyl)]-ferrocene therefrom by eluting with ethylene chloride and 2% methanol in ethylene dichloride; and
   h. recovering 1,1-bis[4-(4-ferrocenyl-1,7dihydroxyheptyl)]-ferrocene from the alumina column by eluting with 6% methanol in ethylene dichloride.

* * * * *